(12) United States Patent
Lin et al.

(10) Patent No.: US 9,556,093 B2
(45) Date of Patent: Jan. 31, 2017

(54) METHOD FOR PRODUCING ALKYLPHENOL

(71) Applicant: Chang Chun Petrochemical Co., Ltd., Taipei (TW)

(72) Inventors: Tian-Yuan Lin, Taipei (TW); Shih-Bo Hung, Taipei (TW)

(73) Assignee: Chang Chun Petrochemical Co., Ltd., Taipei (TW)

(*) Notice: Subject to any disclaimer, the term of this patent is extended or adjusted under 35 U.S.C. 154(b) by 0 days.

(21) Appl. No.: 15/001,368

(22) Filed: Jan. 20, 2016

(65) Prior Publication Data

US 2016/0318833 A1     Nov. 3, 2016

(30) Foreign Application Priority Data

Apr. 30, 2015   (TW) .............................. 104113850 A

(51) Int. Cl.
    *C07C 37/00*      (2006.01)
    *C07C 37/86*      (2006.01)

(52) U.S. Cl.
    CPC .................................... *C07C 37/86* (2013.01)

(58) Field of Classification Search
    CPC .................................. C07C 37/14; C07C 37/86
    USPC ............................................................ 568/756
    See application file for complete search history.

(56) References Cited

U.S. PATENT DOCUMENTS 5,019,669 A * 5/1991 Adams .................... B01D 3/009
                                                         585/446
6,642,425 B2 * 11/2003 Winder ...................... C07C 2/66
                                                         585/323

* cited by examiner

*Primary Examiner* — Sikarl Witherspoon
(74) *Attorney, Agent, or Firm* — McCarter & English, LLP; Yu Lu

(57) ABSTRACT

A method for producing alkylphenol is provided. The method includes charging phenol and an olefinic compound into a reaction zone of a reactive distillation tower for a reaction; and separating a product stream containing alkylphenol from the reactive distillation tower, wherein the boiling point of the olefinic compound is lower than that of the phenol, and the phenol is charged into the reactive distillation tower at a charging position located above a position for charging the olefinic compound.

12 Claims, 2 Drawing Sheets

METHOD FOR PRODUCING ALKYLPHENOL

REFERENCE TO RELATED APPLICATION

Figure 1:
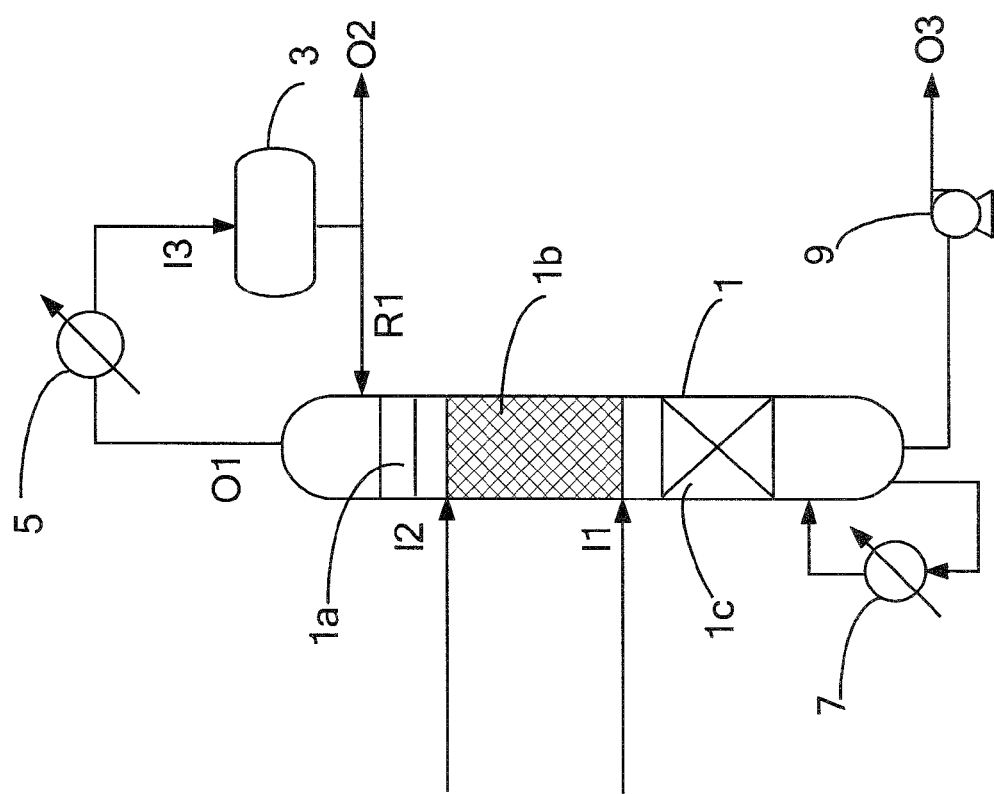

This application claims foreign priority under 35 U.S.C. §119(a) to Patent Application No. 104113850, filed on Apr. 30, 2015, in the Intellectual Property Office of Ministry of Economic Affairs, Republic of China (Taiwan, R.O.C.). The entire content of the above-referenced application is incorporated herein by reference.

BACKGROUND OF THE INVENTION

1. Field of the Invention

The present invention relates to a method for producing alkylphenol, and more particularly, to a method for producing alkylphenol by reactive distillation.

2. Description of Related Art

Alkylated aromatic compounds have several important commercial values. For example, nonylphenol is mainly used to produce nonylphenol polyethoxylates for use as non-ionic surfactants, and can be used as cleansing agents and emulsifiers. Nonylphenol can also be used in the productions of pulp, paint, adhesive agents, leather products, rubber and plastics.

The chemical reactions involving alkylation of aromatic compounds with olefinic compounds have been studied for a long time. Traditionally, phenol and an olefinic compound are charged into a fixed-bed reactor or a stirring reactor for a reaction. However, the temperature is high due to the exothermic reaction; therefore, heat energy needs to be removed from the reactor or the outlet of reactants. Furthermore, the generation of byproducts easily blocks the pores of a catalyst, such that the catalytic activity is decreased. Generally, the charging of an excessive amount of phenol into a reactor is needed to reduce the generation of byproducts, but the energy consumed for subsequent recycling of phenol is increased.

Recently, reactive distillation is also employed to produce an alkylated aromatic compound. For example, CN100337998C discloses the production of alkylated aromatic hydrocarbon by a continuous pressurized reactive distillation process. However, the process still requires a high molar ratio of aromatic hydrocarbon to olefine.

Accordingly, there still exists a need for a method to produce alkylphenol, while still simplifying the steps and saving the energy consumed during the method.

SUMMARY OF THE INVENTION

The present invention provides a method for producing alkylphenol, including reacting in a reactive distillation tower. The reactive distillation tower has a reaction zone for reacting the phenol and olefinic compound charged into the reactive distillation tower, and separating a product stream containing the alkylphenol from the reactive distillation tower. Moreover, the boiling point of the olefinic compound is lower than that of the phenol. Furthermore, when charging phenol and the olefinic compound into the reactive distillation tower, the phenol is charged into the reactive distillation tower at a charging position located above the position for charging the olefinic compound.

According to the method of the present invention, the molar ratio of the charged phenol to the charged nonene can be substantially decreased, such that the conversion of the olefinic compound is 99.9% or above. As such, the subsequent processes of recycling and treating phenol are spared, thereby substantially decreasing energy consumption.

BRIEF DESCRIPTIONS OF THE DRAWINGS

Figure 2:
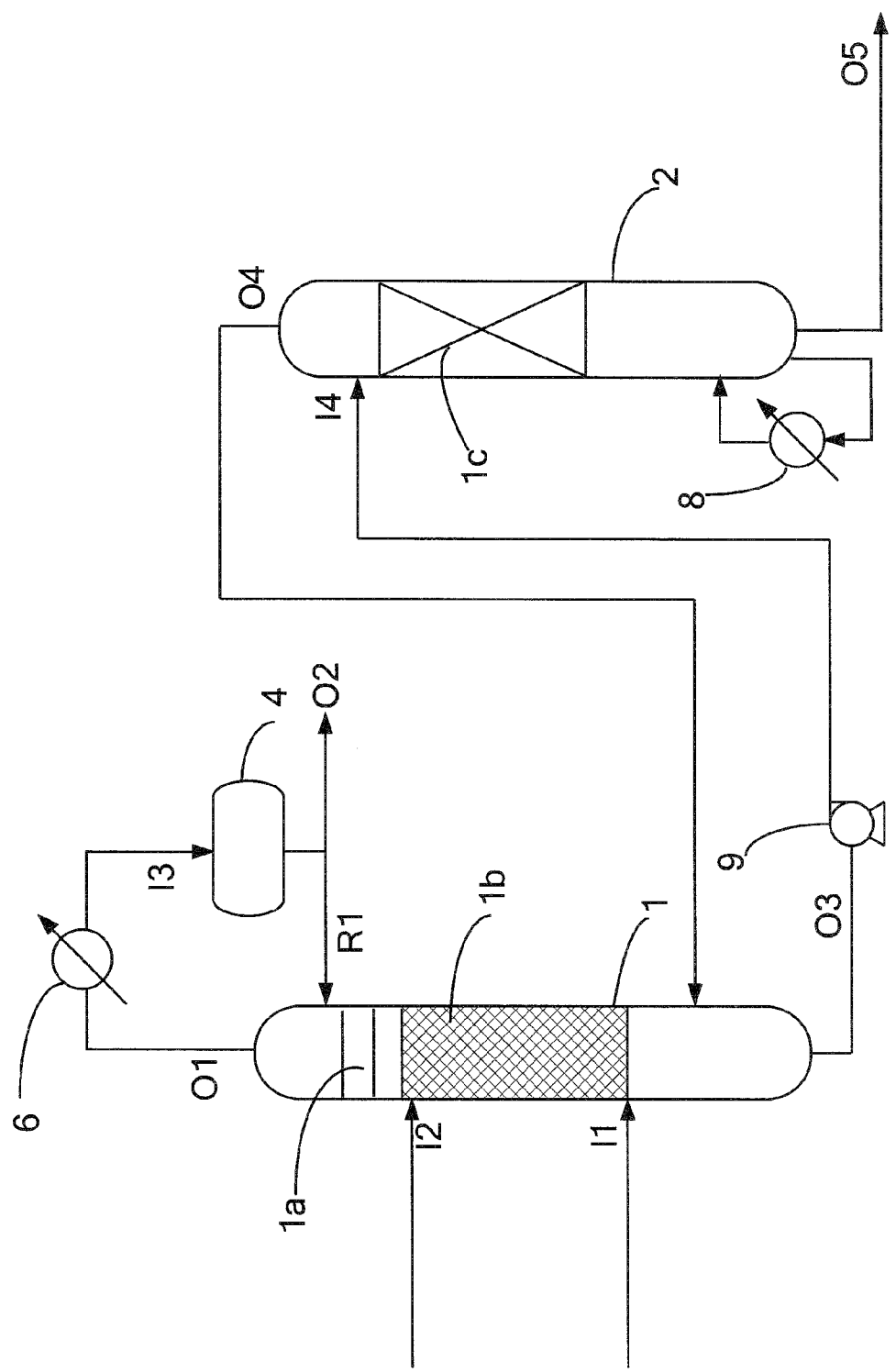

FIG. 1 shows a system for producing alkylphenol according to an embodiment of the present invention; and FIG. 2 shows a system for producing alkylphenol according to another embodiment of the present invention.

DETAILED DESCRIPTION OF THE INVENTION

The following specific embodiments are used to illustrate the detailed description of the present invention, such that a person skilled in the art may readily conceive the advantages and effects of the present invention. The present invention may also be implemented or applied by other different ways of implementation. Each of the details in the present specification may be modified and altered in any way based on different aspects and applications, without departing from the spirit of the present invention.

The structures, proportions, sizes, etc. illustrated in the figures appended to the present specification are all merely used for coping with the content of invention of the present specification, so as to enhance the understanding and perusal of one skilled in the art. They are not used to limit the implemental limitations of the present invention, such that they lack substantial technical meanings. Without affecting the effect brought about and the goals to be achieved by the present invention, any modification of a structure, alteration of a proportion or adjustment of a size should still fall within the scope of the technical content disclosed in the present invention. At the same time, terms, such as "above," "below," "top," "first," "second," "one," etc. used in the present specification, are merely for the clarity of the descriptions, rather than limit the implemental scope of the present invention. Without substantially altering the technical content, an alteration or adjustment of relative positioning can also be regarded as an implemental scope of the present invention.

The present invention provides a method for producing alkylphenol, including charging phenol and an olefinic compound with a boiling point lower than that of the phenol into a reaction zone of a reactive distillation tower, and separating a product stream containing alkylphenol from the reactive distillation tower, wherein the phenol is charged into the reactive distillation tower at a charging position located above a position for charging the olefinic compound.

In the method of the present invention, the reactant stream (e.g., phenol and the olefinic compound) charged into the reactive distillation tower is not pre-treated. Since the boiling point of the olefinic compound charged into the reactive distillation tower is lower than that of the charged phenol, the present invention mainly makes the phenol charged into the reactive distillation tower at a charging position located above a position for charging the olefinic compound. This is to make the phenol and the olefinic compound flow to contact each other in the reaction zone, thereby increasing the conversion of reactants.

In an embodiment of the method for producing alkylphenol, examples of the olefinic compounds with boiling points lower than that of phenol include $C_2$-$C_{10}$ chained olefines and $C_3$-$C_6$ cyclic olefines. In an embodiment, an example of the olefinic compound is nonene.

Moreover, according to the method for producing alkylphenol of the present invention, the phenol and olefinic compound are charged at a molar ratio (i.e., phenol/olefinic compound) of from 1 to 1.5.

It is found in the present invention that when phenol and the olefinic compound are charged into the reactive distillation tower at a molar ratio of 1.1, a comparatively high conversion rate is obtained. If phenol is completely consumed in the reaction zone, the subsequent process of recycling and treating are spared.

In an embodiment for producing alkylphenol, the reaction zone is packed with a solid catalyst; usually, a strong acidic solid catalyst is used, and a preferable solid catalyst is an ion-exchange resin with high temperature stability.

In an embodiment for producing alkylphenol, the product flow is separated from the bottom of the reactive distillation tower.

In another embodiment for producing alkylphenol, a separation tower can be further disposed, and a stripping zone is moved to the separation tower. The product stream can be delivered into the separation tower, and an alkylphenol product can also be obtained from the bottom of the separation tower.

Referring to FIGS. 1 and 2, systems for producing alkylphenol according to the present invention are shown. In the systems illustrated in FIGS. 1 and 2, the reactive distillation tower has two inlets.

As shown in FIG. 1, the system includes the following systematic units: a reactive distillation tower 1, a reflux drum 3, a condenser 5, a reboiler 7, and a pump 9 at the bottom of the tower 1. Moreover, the system includes pipelines, as illustrated in solid lines, for connecting each of the systematic units, so as to connect each of them with fluids.

The reactive distillation unit 1 has a rectification zone 1a, a reaction zone 1b located below the rectification zone 1a and packed with a solid catalyst, a stripping zone 1c below the reaction zone 1b, a first inlet I1, a second inlet I2, a reflux inlet R1, an exit O1 at the top of the tower 1, and an outlet O2, and an outlet O3 at the bottom of the tower 1.

In the method for producing alkylphenol of the present invention, the phenol is charged into the second inlet I2 of the reactive distillation tower 1. The second inlet I2 can be located in the reaction zone 1b or above the reaction zone 1b. The olefinic compound is charged into the first inlet I1 of reactive distillation tower 1. The first inlet I1 can be located in the reaction zone 1b or below the reaction zone 1b. The reboiler 7 is located at the bottom of the reactive distillation tower 1, and the reboiler 7 can heat and vaporize the mixture at the bottom of the tower 1. The exit O1 at the top of the reactive distillation tower 1 is connected to the condenser 5, which can condense most of the gaseous mixture. After the condensation, the mixture is delivered into the reflux drum 3 via the reflux drum inlet I3. Most of the phenolic liquid flows back to the reactive distillation tower 1 via the reflux inlet R1. A small amount of the phenolic fluid is discharged from the outlet O2 or totally refluxed without being discharged. The product of the reaction is taken out from the bottom outlet O3.

The method for producing alkylphenol of the present invention involves simultaneous reaction and distillation in a single reaction in the reactive distillation tower 1. The reaction occurs in the reaction zone 1b (packed with a solid resin catalyst) in the tower, wherein tower plates (not shown) are found in the reaction zone 1b. A plurality of containers are disposed among the tower plates. The containers are each packed with the solid catalyst, wherein the solid catalyst is an ion-exchange resin, such as Purolite series (Purolite), DIAION SK series (Mitsubishi Chemical), and Amberlyst series (Dow Chemical) products. The catalyst within boxes each include an enclosed space and an inlet and an outlet connecting the space for the reaction fluid to flow in and out, thereby providing a longer retention time for the reactants.

In the method for producing alkylphenol of the present invention, the temperature of the reaction zone 1b of the reactive distillation tower 1 is from 80° C. to 150° C. In the method for producing alkylphenol of the present invention, the reaction is carried out in a vacuum environment, for example, the inner pressure of the reactive distillation tower is from 5 torr to 150 torr.

In the method for producing alkylphenol of the present invention, the reflux ratio operated in the top of the reactive distillation tower is from 2 to total reflux.

As shown in FIG. 2, the system differs from the system shown in FIG. 1 in that the stripping zone 1c is moved to the separation tower 2. The number of plates or packings in the stripping zone 1c is theoretically increased, wherein the separation tower 2 has a reboiler 8, and an inlet I4 above the stripping zone 1c, an outlet O4 and another outlet O5.

EXAMPLE

Example 1

Firstly, nonene was charged into the reactive distillation tower 1 via the first inlet I1, and phenol was charged into the reactive distillation tower 1 via the second inlet I2. The phenol and the nonene were charged at a molar ratio of 1.5. The reboiler 7 was disposed at the bottom of the reactive distillation tower 1. The reboiler 7 could heat and vaporize the reaction mixture at the bottom of the tower. Alkylation occurred between the phenol and nonene in the reaction zone 1b. The catalytic boxes in the reaction zone 1b were each packed with an ion-exchange resin (Amberlyst 36). The outlet O1 at the top of the tower 1 was connected to the condenser 5, which could condense most of the gaseous mixture. After the condensation, the mixture was delivered into the reflux drum 3 via the reflux drum inlet I3. Most of the phenolic liquid was flowed back to the reactive distillation tower 1 via the reflux inlet R1. A small amount of the phenolic fluid was discharged from the outlet O2 or totally reflux without being discharged. The product of the reaction was taken out from the bottom outlet O3. The composition of the product is listed below in Table 1.

Example 2

Alkylation between phenol and nonene occurred in the same manner as in example 1, wherein the phenol and the nonene were charged at a molar ratio that was changed to 1.1. The composition of the product is listed below in Table 1.

Comparative Example 1

The phenol and the nonene were charged at a molar ratio of 1.8 and mixed, and then entered into a fixed-bed reactor. In this comparative example, a total of 5 reactors connected in series were used. The operating temperature changed from 120° C. in the first reactor to the operating temperature of 50° C. in the fifth reactor. The results of the examples are listed below in Table 1.

|  | Example 1 | Example 2 | Comparative example 1 |
|---|---|---|---|
| Amount charged | 6.4 tons/hour | 5.3 tons/hour | 8.2 tons/hour |
| Molar ratio of phenol/nonene charged | 1.5 | 1.1 | 1.8 |
| Total number of theoretical plates | 20 | 20 | — |
| Theoretical plate numbers in a reaction zone | 9 | 9 | — |
| Number of fixed bed reactors | — | — | 5 |
| Reacting Temperature | 80 to 140° C. | 80 to 150° C. | 50 to 120° C. |
| Pressure at the top of a tower | 10 torr | 10 torr | — |
| Pressure at the bottom of a tower | 110 torr | 110 torr | — |
| Reflux ratio | Total reflux | Total reflux | — |
| Operating temperature of reboiler | 180° C. | 193° C. | — |
| Composition at the bottom of a reactive distillation tower or an outlet of the reactor | Nonene: 30 ppm Phenol: 18.2 wt % Nonylphenol: 79.4 wt % Dinonylphenol: 2.4 wt % | Nonene: 10 ppm Phenol: 4.8 wt % Nonylphenol: 92.3 wt % Dinonylphenol: 2.9 wt % | Nonene: 0.5 wt % Phenol: 29.7 wt % Nonylphenol: 61.6 wt % Dinonylphenol: 3.7 wt % |
| Conversion rate of nonene | >99.9% | >99.9% | 92% |
| Steam consumption for production of one ton of nonylphenol | 0.38 ton | 0.35 ton | 0.53 ton |

According to the production method of the present invention, nearly all of the nonene charged are converted, and only a small amount of phenol needs to be recycled. The production method of the present invention can substantially decrease the molar ratio of the charged phenol to the charged nonene, such that the subsequent processes of recycling and treating unreacted phenol are spared, thereby substantially decreasing energy consumption while maintaining a relatively high conversion rate of nonene.

The above examples are provided only to illustrate the principle and effect of the present invention, and they do not limit the scope of the present invention. One skilled in the art should understand that, modifications and alterations can be made to the above examples, without departing from the spirit and scope of the present invention. Therefore, the scopes of the present invention should be accorded to the invention of the appended claims.

We claim:

1. A method for producing alkylphenol, comprising:
   charging phenol and an olefinic compound with a boiling point lower than a boiling point of the phenol into a reaction zone of a reactive distillation tower for a reaction; and
   separating a product stream containing the alkylphenol from the reactive distillation tower,
   wherein the phenol is charged into the reactive distillation tower at a charging position located above a position for charging the olefinic compound, and the molar ratio of the charged phenol to the charged olefinic compound is from 1 to 1.5.

2. The method of claim 1, wherein the phenol is charged into the reaction zone of the reactive distillation tower, or charged into the reactive distillation tower at a position above the reaction zone of the reactive distillation tower.

3. The method of claim 1, wherein the olefinic compound is charged into the reaction zone of the reactive distillation tower, or charged into the reactive distillation tower at a position below the reaction zone of the reactive distillation tower.

4. The method of claim 1, wherein the product stream is separated from a bottom of the reactive distillation tower.

5. The method of claim 1, wherein the reaction zone is packed with a solid catalyst.

6. The method of claim 5, wherein the solid catalyst is an ion-exchange resin.

7. The method of claim 1, wherein the olefinic compound is selected from the group consisting of $C_2$-$C_9$ chain olefins and $C_3$-$C_9$ cyclic olefins.

8. The method of claim 7, wherein the olefinic compound is nonene.

9. The method of claim 1, wherein the reaction takes place in a vacuum environment.

10. The method of claim 9, wherein an inner pressure of the reactive distillation tower is from 5 torr to 150 torr.

11. The method of claim 1, wherein a temperature of the reaction zone of the reactive distillation tower is from 80° C. to 150° C.

12. The method of claim 1, wherein a reflux ratio at a top of the reactive distillation tower is from 2 to total reflux.

* * * * *